United States Patent
Hora et al.

(10) Patent No.: US 9,725,674 B2
(45) Date of Patent: *Aug. 8, 2017

(54) BLOWN CORN STILLAGE OIL

(71) Applicant: Cargill, Incorporated, Wayzata, MN (US)

(72) Inventors: Michael John Hora, Marion, IA (US); Frank P. Lochel, Delano, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,330

(22) Filed: Dec. 17, 2015

(65) Prior Publication Data

US 2016/0102270 A1   Apr. 14, 2016

Related U.S. Application Data

(62) Division of application No. 14/294,447, filed on Jun. 3, 2014, now Pat. No. 9,243,208, which is a division of application No. 13/321,768, filed as application No. PCT/US2010/035759 on May 21, 2010, now Pat. No. 8,765,985.

(60) Provisional application No. 61/180,664, filed on May 22, 2009.

(51) Int. Cl.
| | | |
|---|---|---|
| C11B 3/08 | (2006.01) | |
| C11B 3/14 | (2006.01) | |
| C07C 29/76 | (2006.01) | |
| C11C 3/00 | (2006.01) | |
| C11B 3/02 | (2006.01) | |

(52) U.S. Cl.
CPC ............ *C11B 3/08* (2013.01); *C07C 29/76* (2013.01); *C11B 3/02* (2013.01); *C11B 3/14* (2013.01); *C11C 3/006* (2013.01)

(58) Field of Classification Search
None
See application file for complete search history.

(56) References Cited

U.S. PATENT DOCUMENTS

| | | |
|---|---|---|
| 1,790,494 A | 1/1931 | Adams et al. |
| 2,396,129 A | 3/1942 | Rodman |
| 2,569,124 A | 9/1951 | Christenson et al. |
| 2,657,224 A | 10/1953 | Bierke |
| 4,330,625 A | 5/1982 | Miller et al. |
| 4,552,775 A | 11/1985 | Baeling et al. |
| 4,650,598 A | 3/1987 | Roberts et al. |
| 5,512,313 A | 4/1996 | Cooper et al. |
| 6,312,826 B1 | 11/2001 | Shogren |
| 6,443,661 B1 | 9/2002 | Wathen |
| 6,476,244 B2 | 11/2002 | Mahlum |
| 6,589,442 B1 | 7/2003 | Wilson et al. |
| 6,759,542 B2 | 7/2004 | Mahlum |
| 6,822,105 B1 | 11/2004 | Luxem et al. |
| 7,262,311 B2 | 8/2007 | Christianson et al. |
| 7,601,858 B2 | 10/2009 | Cantrell et al. |
| 7,608,729 B2 | 10/2009 | Winsness et al. |
| 7,989,647 B2 | 8/2011 | Geiger et al. |
| 8,008,516 B2 | 8/2011 | Cantrell et al. |
| 8,580,988 B2 | 11/2013 | Hora et al. |
| 9,243,209 B2 * | 1/2016 | Lochel .................. C11B 13/00 |
| 2004/0087808 A1 | 5/2004 | Prevost et al. |
| 2006/0107859 A1 | 5/2006 | Sampel |
| 2007/0004811 A1 | 1/2007 | Bruner et al. |
| 2007/0089356 A1 | 4/2007 | Krasutsky et al. |
| 2007/0260080 A1 | 11/2007 | Lee et al. |
| 2008/0190567 A1 | 8/2008 | Winsness |
| 2008/0299632 A1 | 12/2008 | Winsness et al. |
| 2009/0076913 A1 | 3/2009 | Morgan |
| 2009/0123609 A1 | 5/2009 | Harris et al. |
| 2009/0287007 A1 | 11/2009 | Abraham et al. |
| 2010/0036177 A1 | 2/2010 | Ward |
| 2011/0054098 A1 | 3/2011 | Tutin et al. |
| 2012/0065414 A1 | 3/2012 | Lochel |
| 2012/0065417 A1 | 3/2012 | Hora et al. |
| 2013/0065803 A1 | 3/2013 | Hora et al. |

FOREIGN PATENT DOCUMENTS

| | | |
|---|---|---|
| WO | 01/62880 | 8/2001 |
| WO | 2007/088421 | 8/2007 |
| WO | 2010/135637 | 11/2010 |

OTHER PUBLICATIONS

Edgar S. Lower, "Blown (air oxidised) vegetable & marine oils & paint manufacture," Pigment and Resin Technology, May 1987, pp. 7-10.

N. Singh & M. Cheryan, "Extraction of Oil From Corn Distillers Dried Grains and Solubles," Transactions of the ASAE, 1998 American Society of Agricultural Engineers, vol. 41, pp. 1775-1777.

Sievers, A. F., et al., "The preparatin of an edible oil from crude corn oil," 1922, USDA, Bulletin No. 1010, pp. 1-25 (26 pages).

* cited by examiner

*Primary Examiner* — Yate K Cutliff

(57) ABSTRACT

Blown corn stillage oils and methods for making blown corn stillage oils are disclosed. In one aspect the corn stillage oils are stripped to reduce the acid value of the resulting blown, stripped corn stillage oil. The method includes heating a corn stillage oil to a temperature of at least 90° C., and passing air through the heated oil to produce a blown corn stillage oil having a viscosity of at least 50 cSt at 40° C. In one aspect, the blown corn stillage oil is stripped to reduce the acid value of the blown, stripped corn stillage oil to 5 mg KOH/gram or less.

15 Claims, No Drawings

BLOWN CORN STILLAGE OIL

CROSS REFERENCE TO RELATED APPLICATION

This application is a divisional of U.S. patent application, Ser. No. 14/294,447, filed Jun. 3, 2014, entitled BLOWN CORN STILLAGE OIL, which is a divisional of Ser. No. 13/321,768, filed 21 Nov. 2011, entitled BLOWN CORN STILLAGE OIL, which is a national stage entry of International Patent Application No. PCT/US2010/35759, filed 21 May 2010, entitled BLOWN CORN STILLAGE OIL, which application claims the benefit of U.S. Provisional Patent Application No. 61/180,664, filed 22 May 2009, entitled BLOWN CORN STILLAGE OIL, which applications are hereby incorporated by reference in their entirety.

FIELD

The present disclosure relates to blown corn stillage oil and in some aspects blown, stripped corn stillage oils. The disclosure also relates to methods for making such oils

BACKGROUND

Ethanol production from corn has increased in recent years. The corn is typically ground to a course powder that is then mixed with water and yeast and fermented to produce a fermented mixture (sometimes referred to as "mash") that contains residual solids, ethanol and other liquids. The other liquids include water, monoglycerides, diglycerides, triglycerides, glycerin, and free fatty acids. Typically, the liquid portion of the mash is heated to distill off the ethanol, which is captured and sold as an additive for automotive fuels.

The residual liquid remaining after the ethanol is removed contains free fatty acids and glycerol, and from 1% to 3% by weight monoglycerides, diglycerids, triglycerides. The residual liquid from the distillation has generally been sold together with the solids portion of the mash as "distillers dry grain." The distillers dry grain generally is used as feed for livestock.

SUMMARY

The inventors have surprisingly discovered that the monoglycerides, diglycerides, triglycerides, free fatty acids, and glycerol (hereinafter collectively referred to as "corn stillage oil") can be recovered from the other residual liquids of the distillation process by suitable means, preferably by centrifugation of the residual material remaining after the ethanol has been distilled off Centrifugation typically recovers twenty five percent of the corn stillage oil originally present in the residual material being centrifuged.

The corn stillage oil recovered by centrifugation typically: has an acid value from 16 to 32 mg KOH/gram, preferably from 18 to 30 mg KOH/gram; has an iodine value from 110 to 120 g $I_2$/100 g sample; and contains from 0.05 to 0.29 percent by weight monoglycerides, from 1.65-7.08 percent by weight diglycerides, from 70.00 to 86.84 percent by weight triglycerides, from 8 to 16 percent by weight (for example, from 9 to 15 percent by weight) free fatty acids, and from 0.00 to 0.20 weight percent glycerin. Typically, the corn stillage oil has from 53 to 55 percent by weight groups derived from diunsaturated fatty acids, from 39 to 43 percent by weight groups derived from monounsaturated fatty acids, from 15 to 18 percent by weight groups derived from saturated fatty acids, and from 1 to 2 percent by weight groups derived from triunsaturated fatty acids. The groups derived from each of the above fatty acids are present either as groups within the mono-, di-, and tri-glycerides or as free fatty acids.

The free fatty acid content of the corn stillage oil is very high compared to conventional vegetable oils. Surprisingly, the inventors have discovered processes that can be readily used to process the high fatty acid containing stillage oil to provide beneficial products.

One inventive method to process the corn stillage oil is to heat the oil to a temperature of at least 90° C., typically from 90° C. to 125° C., preferably from 100° C. to 120° C., and more preferably from 105° C. to 115° C. and pass air through it (commonly referred to as "sparging") for a desired period of time. This process polymerizes the components of the corn stillage oil and introduces hydroxyl, epoxy functionality and ether linkages. The resulting blown-corn stillage oil can be further processed in order to provide final oil products that can be used in various end-use applications.

In one preferred aspect, the blown-corn stillage oil is stripped to reduce its free fatty acid content and to remove other volatiles from the oil.

In a particularly preferred aspect, the corn stillage oil is blown for a sufficient period of time at an appropriate temperature to produce highly polymerized oil. For example, air is blown (sparged through) the corn stillage oil being maintained at a temperature of from 90° C. to 125° C. (preferably from 100° to 120° C. and more preferably from 105° C. to 115° C.) typically for from 2 to 20 hours (preferably from 3 to 18 hours). The resulting polymerized oil is then relatively heavily stripped. For example, the blown oil is heated to a temperature from 230° C. to 270° C. (preferably from 240° to 260° C.), and in some instances from 235° C. to 245° C., and vacuum stripped at a pressure of 100 torr or less, preferably 75 torr or less, and more preferably 50 torr or less and not preferably 20 torr or less for typically from 8 to 12 hours (preferably from 9 to 11 hours). This stripping reduces the content of free fatty acids and other volatiles such as lower molecular weight glycerides and unexpectedly produces a stripped, blown-corn stillage oil having a very high flash point that can be used for end-use applications such as very high temperature suitable de-dusting fluids. The stripping also typically "Bodies" the oil and further increases its molecular weight and viscosity. "De-dusting fluids" are fluids used for reducing the dust created when a surface is agitated or perturbed. The stripped, blown-corn stillage oil will help minimize the chances of sparking and/or explosions in high flash point environments and will also degrade slower than petroleum based mineral oils having lower flash points. Typically, this oil has a flash point of at least 300° C., preferably at least 310° C., and more preferably at least 320° C.

In another particularly preferred aspect, the corn stillage oil is blown for a relatively shorter period of time to produce an oil that is lightly polymerized. For example, air is blown (sparged through) the corn stillage oil being maintained at a temperature of from 90° C. to 125° C. (preferably from 100° to 120° C., and more preferably from 105° to 115° C.) typically for from 2 to 10 hours (preferably from 3 to 8 hours). The lightly polymerized oil is then relatively heavily stripped to reduce the content of free fatty acids and other volatiles within the oil. For example, the blown oil is heated to a temperature from 230° C. to 270° C. (preferably from 240° to 260° C.) and vacuum stripped at a pressure of 100 torr or less, preferably 75 torr or less, and more preferably 50 torr or less typically for from 8 to 12 hours (preferably from 9 to 11 hours). This stripped, blown-corn stillage oil has an unexpectedly low pour point, typically less than −14° C. This low pour point oil is particularly useful for low temperature de-dust applications and for use in Bar & Chain lubricant end-use applications. Examples of end-use applications include many areas where petroleum based oils are used such as: chain saw lubricant applications and other applications that utilize bar, chain, and sprockets that demand medium viscosity oils to provide adequate lubrication. This blown and stripped oil can also be used in metal forming operations such as drawing, in hydraulic systems as a base fluid and in 2 cycle engine oil formulations. Examples of de-dust applications where relatively low pour points oils as described here are useful include: fertilizer plants where fertilizer is transferred outdoors in winter temperatures and rock crushing applications where dust is a concern. If a lower pour point is desired, additives such as a heavily blown linseed oil (such as the blown linseed oil available from Cargill, Incorporated under the trademark VOM 25), or diesters having a crystallization temperature less than −28.9° C., preferably less than −34° C., more preferably less than −40° C. and further more preferably less than −45° C. and in some instances less than −54° C. (such as his (2-ethylhexyl) adipate) can be blended with the low pour point oil to produce a very low pour point oil having a pour point typically less than −23° C. and preferably less than −26° C.

Surprisingly, the inventor has discovered that a titre (as described below) typically is reduced to less than one percent by weight (1 wt %) by heating the corn stillage oil during the blowing.

DETAILED DESCRIPTION

"Hash Point" or "Flash Point Temperature" is a measure of the minimum temperature at which a material will initially flash with a brief flame. It is measured according to the method of ASTM D-92 using a Cleveland Open Cup and is reported in degrees Celsius (° C.).

"Pour Point" or "Pour Point Temperature" is a measure of the lowest temperature at which a fluid will flow. It is measured according to the method of ASTM D-97 and is reported in degrees Celsius (° C.).

"Iodine Value" (IV) is defined as the number of grams of iodine that will react with 100 grams of material being measure. Iodine value is a measure of the unsaturation (carbon-carbon double bonds and carbon-carbon triple bonds) present in a material. Iodine Value is reported in units of grams iodine ($I_2$) per 100 grams material and is determined using the procedure of AOCS Cd Id-92.

"Hydroxyl number" (OH#) is a measure of the hydroxyl (—OH) groups present in a material. It is reported in units of mg KOH/gram material and is measured according to the procedure of ASTM E1899-02.

"Acid Value" (AV) is a measure of the residual hydronium groups present in a compound and is reported in units of mg KOH/gram material. The acid number is measured according to the method of AOCS Cd 3d-63.

"Gardner Color Value" is a visual measure of the color of a material. It is determined according to the procedure of ASTM DI544, "Standard Test Method for Color of Transparent Liquids (Gardner Color Scale)". The Gardner Color scale ranges from colors of water-white to dark brown defined by a series of standards ranging from colorless to dark brown, against which the sample of interest is compared. Values range from 0 for the lightest to 18 for the darkest. For the purposes of the invention, the Gardner Color Value is measured on a sample of material at a temperature of 25° C.

Recovery of Corn Stillage Oil

Fermented mash comprising ethanol, water, residual grain solids (including proteins, fats, and unfermented sugars and carbohydrates), and from 1 to 3 percent by weight corn stillage oil is heated to distill and recover ethanol from the fermented mash. Typically, the ethanol is distilled by two methods.

In the first method, the fermented mash is heated to temperatures typically from 76° C. to 99° C. under vacuum typically from 50 to 300 torr (for example from 150 to 250 torr) to distill off the desired ethanol. An example of this first method is the ethanol distillation process available from ICM, Incorporated (hereinafter the "ICM Process").

In the second method, the fermented mash is heated to temperatures typically from 235° F. to 250° F. under pressures typically from 1 to 25 psig (for example from 1 to 15 psig) to distill off the desired ethanol. An example of this second method is the process available from Delta-T Corporation (hereinafter the "Delta-T Process").

For both the first and second method, after the ethanol is distilled off, the remaining liquid portion typically contains from 1 wt % to 4 wt % corn stillage oil. The material remaining after the ethanol is distilled off is typically centrifuged using a centrifun, such as a Westfalia sliding disk centrifuge available from Westfalia Corporation. From 25 wt % to 35 wt % of the corn stillage oil contained in the material is recovered during this centrifugation step. The recovered unprocessed corn stillage oil typically exhibits a Gardner color of 12 or greater, for example, a Gardner color of from 14 to 18.

Corn stillage oil produced from the residual material of the first distillation method is hereinafter referred to as "vacuum distilled corn stillage oil." Corn stillage oil produced from the residual material of the second distillation method is hereinafter referred to as "pressure distilled corn stillage oil." When the corn stillage oil is lightly blown and not stripped, vacuum distilled corn stillage oil is preferably utilized since the resulting blown corn stillage oil will have a lower value for Gardner color than a blown stillage oil made using a pressure distilled corn stillage oil.

Unprocessed corn stillage oil typically exhibits: a viscosity at 40° C. of from 25 to 35 cSt (for example from 28 to 3) cSt) as measured utilizing viscosity tubes in a constant temperature bath as further described below; a viscosity at 100° C. of from 5 to 10 cSt for example from 6 to 9 cSt as measured utilizing viscosity tubes in a constant temperature bath as further described below; a Viscosity Index of from 80 to 236 determined using the procedures and measurement scale established by the Society of Automotive Engineers; a flash point from 220° C. to 245° C., for example from 225° C. to 240° C.; a saponification value of from 170 to 206 mg KOH/g; a pour point typically of from −5° C. to −14° C.; an acid value of from 15 to 33 mg KOH/gram (for example, from 16 to 32 mg KOH/gram); an iodine value from 110 to 125 grams $I_2$/100 grams sample; and from 8 to 16 wt % (for example, from 9 to 15 wt %) free tatty acids.

Viscosity for this invention is measured according to the method of ASTM D445. In this method oil to be tested is placed in a calibrated glass capillary viscometer, which is then placed into a constant temperature bath at the temperature specified. Once thermal equilibrium is reached, the oil is drawn up into the reservoir of the capillary tube. As the fluid drains, it passes the top mark on the tube and a timer is started. When the oil passes the lower mark, the timer is stopped and the flow time is recorded. The recorded flow time is multiplied by a factor which is specific to each viscometer tube. The resultant product of the flow time multiplied by the factor is reported as viscosity in cSt at the test temperature.

Unprocessed corn stillage oil also typically contains two phases at 25° C. The first phase is the liquid phase, which settles toward the top of any container that contains the corn stillage oil. This phase typically is reddish in color. The second phase is a solid that typically settles toward the bottom of any container containing the oil. At 62° C., the second phase tends to dissolve into the liquid phase, but will settle out again if the untreated corn stillage oil is cooled to room temperature. The inventors have determined that the second solid phase typically makes up at least 4 percent by weight (4 wt %) of the total unprocessed corn stillage oil. For example, the second solid phase may make up from 5 wt % to 12 wt % of the unprocessed corn stillage oil. For purposes of this invention, this second solid phase is referred to as the "titre."

Blowing the Corn Stillage Oil

The blowing typically is achieved by sparging air through corn stillage oil heated to from 90° C. to 125° C., preferably from 100° C. to 120° C., and more preferably from 105° C. to 115° C. The vessel containing the corn stillage oil during the blowing step typically is at atmospheric pressure. The pressure of the air being sparged through the oil is generally high enough to achieve the desired air flow through the corn stillage oil. The air is introduced at a sufficient flow rate for a sufficient period of time to achieve the desired viscosity. Typically, the air is introduced into the corn stillage oil at a rate of 0.009 to 0.011 cubic feet per minute per pound of corn stillage oil present. Preferably, the air is dispersed evenly in the vessel to maximize surface area exposure. Typically the vessel will have a distribution ring or spoke-like header to create small volume bubbles evenly within the oil. The duration of sparging air through the corn stillage oil is varied and determined according to the desired properties of the blown oil and the end-use applications for the resulting product.

Surprisingly, the inventors have discovered that the corn stillage oil described above, can be effectively reacted with air to provide blown-corn stillage oil which advantageously has a relatively high level of polymerization, as shown by their increased viscosities at 40° C. and 100° C. (typically above 50 cSt @40° C. preferably above 60 cSt @ 40° C. more preferably above 130 cSt @ 40° C. and in some instances where high molecular weight is particularly desirable, above 5000 cSt @ 40° C.; and (typically above 9 cSt @ 100° C., preferably above 11 cSt @ 100° C., more preferably above 12 cSt @ 100° C., and in some instances where high molecular weight is particularly desirable, above 200 cSt @ 100° C. Typically, the blown corn stillage oils are not stripped of free fatty acids for applications where free fatty acids are a benefit. For example, for applications where boundary lubrication are important, the blown corn stillage oil preferably is not stripped as described below.

Surprisingly, the acid value for the blown corn stillage oil is not significantly increased compared to the acid value for the unblown corn stillage oil. Typically the acid value does not increase when corn stillage oil is blown. Preferably, the blown corn stillage oil comprises relatively no more than 10 relative percent more free fatty acids than the starting unblown corn stillage oil, and more preferably, the free fatty acid content of the blown corn stillage oil is equivalent to the free fatty acid content of the starting corn stillage oil.

That the free fatty acid content of blown corn stillage oil is not significantly higher than the free fatty acid value for the starting unblown corn stillage oil, is unexpected as the acid value for other vegetable oils, such as soybean oil does increase significantly when the oil is blown. For example, a sample of soybean oil with an acid value of less than 0.1 mg KOH/g when blown to a viscosity of 130 cSt @ 40° C. typically has an acid value of 9 to 11 mg KOH/gram, or more. Generally, the acid value of a vegetable oil increases significantly when air is blown into the oil at temperatures above 100° C. As the blown-corn stillage oil does not have significantly higher acid value than the unblown corn stillage oil, the blown corn stillage oil can be effectively stripped of volatiles, such as free fatty acids, using conventional stripping equipment and methods.

Generally, the acid value of a vegetable oil increases significantly when air is blown into the oil at temperatures above 100° C. As the blown-corn stillage oil does not have significantly higher acid value than the unblown corn stillage oil (i.e. acid value from 9 to 32 mg KOH/gram), the blown corn stillage oil can be effectively stripped of volatiles, such as free fatty acids, using conventional stripping equipment and methods.

The reactions that occur during the blowing of the oil increase the molecular weight of the oil, which tends to increase the viscosity of the blown oil versus the unblown oil. Additionally, the blowing process introduces hydroxyl functionality onto the resulting oil, which also tends to increase the viscosity of the oil. The blown-corn stillage oil typically has a hydroxyl number from 8 to 60 mg KOH/gram oil. The higher viscosity (especially at higher temperature) provides the oil with better hydrodynamic lubrication properties.

The inventors also have surprisingly discovered that corn stillage oil can be more readily blown to desired viscosities, such as 70 cSt, than soybean oil under the same blowing conditions. For example, air was sparged through corn stillage oil and soybean oil maintained at 100° C. and atmospheric pressure to determine how long it would take each to build viscosity. As can be seen from Table 1, below, the blown corn stillage oil's viscosity increased much quicker and reached a viscosity of 70.9 cSt at 40° C. in 25.5 hours versus the blown soybean oil, which took 39.5 hours to reach a viscosity of 71.8 cSt at 40° C. under similar conditions. Therefore, it takes at least 20% less time for the blown corn stillage oil to reach approximately 71 cSt at 40° C. than a blown soybean oil to reach a similar viscosity, and in some instances at least 25% less time, preferably at least 30% less time and more preferably at least 35% less time for the blown corn stillage oil to reach a given viscosity at 40° C. than a blown soybean oil under similar blowing conditions.

TABLE 1

| | Viscosity at 40° C. (cSt) | | | | | | | | | | | | | | | |
|---|---|---|---|---|---|---|---|---|---|---|---|---|---|---|---|---|
| | TIME at 100° c. (Hrs) | | | | | | | | | | | | | | | |
| | 0 | 1 | 2.25 | 3.25 | 6.25 | 11 | 12 | 13.25 | 16 | 16.75 | 19 | 21.25 | 23.5 | 25.5 | 32.5 | 39.5 |
| blown, corn stillage oil | 33 | 33 | 33 | 33 | 33 | 39.4 | 39.6 | 39.7 | | 45.9 | 46.7 | 51.4 | 63.8 | 70.9 | | |
| Blown soybean oil | | | | | | | | | 41.7 | | | | 44.5 | | 53.4 | 71.8 |

For high-flash point end-use applications (as described below) for example, high temperature de-dust applications, asphalt viscosity index improvers and open gear lubricants applications, the blowing is continued for a time sufficient to obtain a blown corn stillage oil having a viscosity of: at least 450 cSt at 40° C., preferably at least 500 cSt at 40° C.; and at least 50 cSt at 100° C., preferably at least 55 cSt at 100° C., more preferably at least 70 cSt at 100° C., and in some applications at least 270 cSt (4) 100° C. This will provide for an oil having a viscosity of: at least 500 cSt at 40° C., preferably at least 700 cSt at 40° C., and more preferably at least 730 cSt at 40° C.; and at least 63 cSt at 100° C., preferably at least 68 cSt at 100° C., and more preferably at least 70 cSt at 100° C. after stripping as described, below.

In an alternative aspect, the oil is blown to a lower viscosity, but is allowed to build more viscosity in during the stripping step described below. In this alternative aspect, the blowing is continued for a time sufficient to obtain a blown oil blend having a viscosity of: at least 200 cSt at 40° C., preferably at least 300 cSt at 40° C., and in some instances at least 1500 cSt at 40° C. The blown oil is then stripped (as described below) to sufficiently body the oil to provide a blown, stripped oil having a viscosity of: at least 500 cSt 40° C., preferably at least 700 cSt at 40° C., and more preferably at least 730 cSt at 40° C., and in some instances at least 5000 cSt at 40° C.

For large size reactors, for example reactors able to blow 45,000 pounds of oil, even with good dispersion and small volume air bubbles, it may take longer (from 30 to 40 hours) to blow the oil to the desired viscosity (when the oil is at a temperature of from 105° C. to 115° C. at atmospheric pressure, at the rates described above, to achieve these desired viscosities. Longer sparging times typically will be necessary if the air is not evenly dispersed within the oil and/or the volume of the air bubbles are relatively larger.

For agricultural adjuvant use, de-dust fluids, metalworking oils, and as additives to lower the softening point of asphalt the blowing is continued for a time sufficient to obtain a blown corn stillage oil having a viscosity of: at least 50 cSt at 40° C., preferably at least 60 cSt at 40° C.; and at least 10 cSt at 100° C., preferably at least 13 cSt at 100° C. This will provide an oil having a viscosity of at least 50 cSt at 40° C., preferably at least 60 cSt at 40° C.; and at least 10 cSt at 100° C., preferably at least 13 cSt at 100° C. With even dispersion and small volume air bubbles, air typically is sparged through the oil for from 2 to 8 hours (when the oil is at a temperature of from 105° C. to 115° C. at atmospheric pressure, at the rates described above, to achieve these desired viscosities. Longer sparging times typically will be necessary if the air is not evenly dispersed within the oil and/or the volume of the air bubbles are relatively larger. For large size reactors, for example reactors able to blow 45,000 pounds of oil, even with good dispersion and small volume air bubbles, it may take longer (from 20 to 30 hours) to blow the oil to the desired viscosity (when the oil is at a temperature of from 105° C. to 115° C. at atmospheric pressure, at the rates described above, to achieve these desired viscosities. Longer sparging times typically will be necessary if the air is not evenly dispersed within the oil and/or the volume of the air bubbles are relatively larger.

For low pour point applications (as described below) the blowing is continued for a time sufficient to obtain a blown corn stillage oil having a viscosity of: at least 60 cSt at 40° C., preferably at least 140 cSt at 40° C.; and at least 12 cSt at 100° C., preferably at least 14 cSt at 100° C. This will provide an oil having a viscosity of at least 60 cSt at 40° C., preferably at least 140 cSt at 40° C.; and at least 12 cSt at 100° C., preferably at least 14 cSt at 100° C. The blown corn stillage oil for these applications typically have a viscosity of: less than 500 cSt at 40° C., preferably less than 400 cSt at 40° C., and more preferably less than 250 cSt at 40° c.; and less than 56 cSt at 100° C., and preferably less than 43 cSt at 100° C. and more preferably less than 29 cSt at 100° C. With even dispersion and small volume air bubbles, air typically is sparged through the oil for from 2 to 10 hours, preferably from 3 to 8 hours (when the oil is at a temperature of from 105° C. to 115° C. at atmospheric pressure, at the rates described above), to achieve these desired viscosities. Longer sparging times typically will be necessary if the air is not evenly dispersed within the oil and/or the volume of the air bubbles are relatively larger. For large size reactors, for example reactors able to blow 45,000 pounds of oil, even with good dispersion and small volume air bubbles, it may take longer (from 20 to 40 hours) to blow the oil to the desired viscosity (when the oil is at a temperature of from 105° C. to 115° C. at atmospheric pressure, at the rates described above, to achieve these desired viscosities. Longer sparging times typically will be necessary if the air is not evenly dispersed within the oil and/or the volume of the air bubbles are relatively larger.

Optionally, a catalyst may be used in some embodiments to enhance the blowing of the oil. Examples of catalysts that may be useful include peroxides, and catalysts comprising metals selected from the group consisting of Transition Elements and Group IV metals as described in "McGraw-Hill Dictionary of Scientific and Technical Terms," Appendix 7 (Fifth Edition 1994).

Further examples of catalysts that may be useful for enhancing the blowing procedure include catalysts comprising metals related from the group consisting of: tin, cobalt, iron, zirconium, titanium and combinations thereof.

Stripping the Blown-Corn Stillage Oil

The blown-corn stillage oil is stripped by vacuum stripping. The pressure during the stripping typically is less than 100 torr, preferably less than 75 torr, and more preferably 50 torr or less. As mentioned above, the temperature during the stripping step typically is from 230° C. to 270° C., preferably from 240° C. to 260° C. The stripping will lower the content of free fatty acids in the oil and therefore reduce the acid value of the resulting stripped oil. Typically, the oil is sufficiently stripped to reduce the acid value of the resulting stripped blown-corn stillage oil to 5 mg KOH/g or less, preferably 4 mg KOH/g or less, and in some instances, such as where the oil is intended for high flash point end-use applications, less than 3.5 mg KOH/g preferably less than 3.0 mg KOH/g and even more preferably 2.8 mg KOH/g or less. Stripping the oil will also increase the viscosity of the resulting oil compared to the non-stripped oil and will increase the flash point of resulting oil. Typically, the oil is vacuum stripped for a period of from 8 to 12 hours, preferably from 9 to 11 hours. For large size reactors, for example reactors able to strip 45,000 pounds of oil, it may take longer (from 20 to 60 hours) to strip the blown oil to the acid value (typically 5.0 mg KOH/gram or less, preferably 3.5 mg KOH/gram or less, and in some instances 3.0 mg KOH/gram or less and preferably 2.8 mg KOH/gram or less. In an alternative embodiment, the inventors have surprisingly discovered that when it is necessary to reduce the acid value to particularly low levels (for example to values of 3.5 mg KOH/gram or less), it may be advantageous to optionally add small amounts of a polyol, such as glycerol, to the blown-corn stillage oil being stripped.

In a first preferred aspect of this alternative embodiment, the blown-corn stillage oil is stripped using nitrogen or vacuum stripping until the acid value of the oil is reduced to from 5 mg KOH/gram to about 9 mg KOH/gram, preferably from about 7 mg KOH/gram to about 9 mg KOH/gram. Then a polyol, preferably glycerin is added to the oil and the oil is stripped until the acid value of the oil is less than 5.0, preferably until the acid value is 3.5 mg KOH/gram or less, and in some instance 3.0 mg KOH/gram or less or 2.8 mg KOH/gram or less. During this final stripping stage, a nitrogen purge preferably is maintained on the oil to assist in the removal of volatiles from the oil, including water that may be liberated by the reaction of glycerin with fatty acids. However, during this final stripping state a vacuum preferably is no longer maintained on the vessel containing the oil. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown-corn stillage oil is allowed to cool. In this aspect the final hydroxyl number of the blown-corn stillage oil is typically less than 50 mg KOH/gram, preferably less than 40 mg KOH/gram, and in some instances less than 30 mg KOH/gram, for example from about 23 to 29 mg KOH/gram. If a higher viscosity oil is desired, the viscosity of the blown-corn stillage oil typically is at least about 500 cSt at 40° C., preferably at least 700 at 40° C., more preferably at least 730 cSt at 40° C., and in some instances at least 5000 cSt at 40° C. If a relatively lightly polymerized oil is desired, the viscosity of the blown-corn stillage oil is from 60 cSt to 200 cSt at 40° C.

The amount of polyol added to the blown-corn stillage oil in this first preferred aspect typically is sufficient to obtain a ratio of moles of hydroxyl groups added to fatty acid groups in the blown oil of from about 1:5 to less than about 1:1, preferably from about 1:4 to about 9:10, more preferably from about 2:5 to about 4:5; and further more preferably from 1:2 to 4:5.

In a second preferred aspect of this alternative embodiment, the polyol is added at the beginning or soon after stripping of the blown-corn stillage oil has commenced. In this second preferred aspect, the temperature of the blown-corn stillage oil is as described above. Typically, sufficient polyol (preferably glycerin) is added to the blown-corn stillage oil to obtain a ratio of moles of hydroxyl groups added per mole of fatty acids groups present in the oil of from about 1:1 to about 2:1, preferably from about 1.6:1 to about 1.9:1, and more preferably from about 1.75:1 to about 1.85:1. During this aspect, nitrogen is sparged through the oil, typically at a rate of from about 5 to 10 cfm per 45000 pounds mass oil. Preferably, during this aspect a vacuum is not applied to the oil. Nitrogen is sparged through the oil until the acid value of the oil is less than 5 mg KOH/gram, preferably less than 3.5 mg KOH/gram and in some instances 3M mg KOH/gram and even 2.8 mg KOH/gram. Once the acid value has been reduced to the desired value, the heat may be removed if the desired viscosity has been obtained. If the desired viscosity has not been reached, the oil will continue to be heated until the desired value for viscosity is obtained. After the desired acid value and viscosity have been obtained, the blown-corn stillage oil is allowed to cool. If a higher viscosity oil is desired, the viscosity of the blown-corn stillage oil typically is at least about 500 cSt at 40° C., preferably at least 700 at 40° C., more preferably at least 730 cSt at 40° C., and in some instances at least 5000 cSt at 40° C. If a relatively lightly polymerized oil is desired, the viscosity of the blown-corn stillage oil is from 60 cSt to 200 cSt at 40° C.

End-Use Applications

Low Pour Point Applications

For end-use applications requiring low pour point temperatures, the stripped, blown-corn stillage oil typically exhibits a pour point of lower than −9° C., preferably lower than −10° C., and in some instances −14° C. or lower. Examples of end use applications where low pour point is beneficial include, for example low temperature de-dust fluids (for example, fertilizer plants where fertilizer is transferred outdoors in winter temperatures and rock crushing applications where dust is a concern), bar & chain lubricant fluids (such as, chain saw lubricant applications and other applications that utilize bar, chain, and sprockets that demand medium viscosity oils to provide adequate lubrication), and asphalt softening point modifiers.

A stripped, blown-corn stillage oil formulation exhibiting even lower pour point can be made by blending from 5 to 7 weight percent of a heavily blown linseed oil (such as the heavily blown linseed oil available from Cargill, Incorporated under the trade designation VOM25) or diesters having a crystallization temperature less than −28.9° C., preferably less than −34° C., more preferably less than −40° C. and further more preferably less than −45° C. and in some instances less than −54° C. (such as his (2-ethylhexyl) adipate). The pour point of blown, stripped corn stillage oil blended with a heavily blown linseed oil and/or a diester as described above may have a pour point less than −23° C. and preferably less than −26° C. Preferably, both a blown linseed oil and a diester, both as described above, are utilized to lower the pour point of the blown, stripped corn stillage oil. These oils are particularly useful for use in bar and chain lubrication end-use applications.

VOM25 has a viscosity of 44,000 cSt @ 40° C. and an acid value of ≤3 milligram KOH/gram material.

For low pour point applications, the corn stillage oil typically is blown for a relatively shorter period of time to produce an oil that is lightly polymerized. For example, air is blown (sparged through) the corn stillage oil being maintained at a temperature of from 90° C. to 125° C. (preferably from 100° to 120° C., and more preferably from 105° to 115° C.) typically for from 2 to 10 hours (preferably from 3 to 8 hours). The lightly polymerized oil is then relatively heavily stripped to reduce the content of free fatty acids and other volatiles within the oil. For example, the blown oil is heated to a temperature from 230° C. to 270° C. (preferably from 240° to 260° C.) and vacuum stripped at a pressure of 100 torr or less, preferably 75 torr or less, and more preferably 50 torr or less typically for from 8 to 12 hours minutes (preferably from 9 to 11 hours).

This blown and stripped oil can also be used in metal forming operations such as drawing, in hydraulic systems as a base fluid and in 2 cycle engine oil formulations.

High-flash Point Applications

High flash point applications often expose lubricating oil to temperatures above 500° F., often above 550° F. and in some instance temperature up to and/or above 600° F. Petroleum-based oils generally do not have flash point temperatures high enough to safely operate in this type of environments. Also, the petroleum-based oils may break down and rapidly oxidize and in a worse case scenario may burn in these types of environments. The inventors have surprisingly found that by heavily blowing the corn stillage oil its molecular weight and viscosity can be increased sufficiently to be able to operate effectively in end-use applications requiring such high flash points once the resulting blown corn stillage oil has been stripped to reduce the acid value to 3.5 mg KOH/g or less, preferably 3.0 mg KOH/g or less, and more preferably 2.8 mg KOH/g or less.

In a particularly preferred aspect, the corn stillage oil is blown for a sufficient period of time at an appropriate temperature to produce highly polymerized oil. For example, air is blown (sparged through) the corn stillage oil being maintained at a temperature of from 90° C. to 125° C. (preferably from 100° to 120° C., and more preferably from 105° C. to 115° C.) typically for from 2 to 10 hours (preferably from 3 to 8 hours). For large size reactors (for example reactors able to blow 45,000 pounds of oil), the time period may be longer as described above. The resulting polymerized oil is then relatively heavily stripped. For example, the blown oil is heated to a temperature from 230° C. to 270° C. (preferably from 240° to 260° C.) and vacuum stripped at a pressure of 100 torr or less, preferably 75 torr or less, more preferably 50 torr or less, and not preferably 20 tons or less for typically from 8 to 12 hours (preferably from 9 to 11 hours). For large size reactors (for example reactors able to strip 45,000 pounds of oil), the time period may be longer as described above. This stripping reduces the content of free fatty acids and other volatiles such as lower molecular weight glycerides and unexpectedly produces a stripped, blown-corn stillage oil having a very high flash point that can be used for end-use applications such as very high temperature suitable de-dusting fluids. The stripped, blown-corn stillage oil will help minimize the chances of sparking and/or explosions in high flash point environments and will also degrade slower than petroleum based mineral oils having lower flash points. Typically, the blown, stripped corn stillage oil for high-flash point applications has a flash point of at least 300° C., preferably at least 310° C., and more preferably at least 320° C.

Typically, the high-flash point stripped, blown-corn stillage oil typically exhibits a pour point of lower than 0° C., preferably lower than negative 5° C. This combination of high flash point and relatively low pour point is unexpected and is believed to result from the stripped, blown corn stillage oil having a relatively narrow molecular weight distribution with completely randomized molecular structures compared to petroleum base oils. This provides an oil that remains flowable at relatively low temperatures, while still exhibiting good viscosity and lubrication at high temperatures and a high flash point, as described above.

Examples of end-use applications that require such high flash points oils include, but are not limited to: asphalt modification end-use applications and as high temperature de-dusting fluids utilized in high temperature de-dust applications. "De-dusting fluids" are fluids used for reducing the dust created when a surface is agitated or perturbed.

EXAMPLES

The following examples are presented to illustrate the present invention and to assist one of ordinary skill in making and using the same. The examples are not intended in any way to otherwise limit the scope of the invention.

Example 1

Production of Vacuum Distilled Corn Stillage

The vacuum distilled corn stillage oil of example 1 is made according to the ICM Process. This process exposes the fermented corn mash to temperatures of about 82.2° C. under a vacuum from about 50 to about 300 torr to distill off ethanol. The corn stillage oil is recovered by centrifuging the materials remaining after the distillation to recover the vacuum distilled corn stillage oil. The properties of the vacuum distilled corn stillage oil is set forth below in Table 2. While not measured, the vacuum distilled corn stillage oil is believed to contain from about 5 to about 12 percent by weight titre.

TABLE 2

| Properties of Vacuum Distilled Corn Stillage Oil | |
|---|---|
| Sample No. | 2-1 |
| 40° C. Viscosity (cSt) | 31 |
| 100° Viscosity (cSt) | 8 |
| Viscosity Index | 249 |
| Flash Point (° C.) | 238 |
| Saponification Value (mg KOH/g) | 202 |
| Pour Point Temperature (° C.) | −7 |
| Acid Value (mg KOH/grams) | 22.2 |
| Free Fatty Acid (wt %) | 11.1 |
| Iodine value (gram $I_2$/100 grams) | 122 |
| Gardner Color | 15 |
| Hydroxyl number (mg KOH/gram) | 9 |

Example 1a

Production of Pressure Distilled Corn Stillage Oil

The pressure distilled corn stillage oil of example 1a is made according to the Delta T Process. In this process the fermented corn mash is exposed to temperatures of about 235° F. to 250° F. at pressures of from about 1 psig to about 15 psig to distill off ethanol. The pressure distilled corn stillage oil is recovered by centrifuging the material remaining after the distillation to recover the pressure distilled corn stillage oil. The properties of the pressure distilled corn stillage oil is set forth below in Table 2a. While not measured, the pressure distilled corn stillage oil is believed to contain from about 5 to about 12 percent by weight titre, TABLE 2a Properties of Pressure Distilled Corn Stillage Oils

| Sample No. | 2-1a |
|---|---|
| 40° C. Viscosity (cSt) | 31 |
| 100° Viscosity (cSt) | 8 |
| Viscosity Index | 249 |
| Flash Point (° C.) | 238 |
| Saponification Value (mg KOH/g) | 202 |
| Pour Point Temperature (° C.) | −7 |
| Acid Value (mg KOH/gram) | 23 |
| Free Fatty Acid (wt %) | 11.5 |
| Iodine value (gram $I_2$/100 grams) | 118 |
| Gardner Color | 16 |
| Hydroxyl number (mg KOH/gram) | 9 |

Example 2

Blowing the Corn Stillage Oil

Into a 2000 milliliter glass reactor equipped with a stirrer, a heating mantel, a temperature regulator and air blowing tubes, 1200 grams of corn stillage oil, as indicated in Table 3, is charged. The corn stillage oil is heated to the temperatures indicated in Table 3. Air is sparged through the oil as it is heated. The air is sparged through the oil at a rate that maximizes the rate while at the same time causes a relatively even distribution of air bubbles within the oil. The rate of sparging is generally limited by the volume of the reactor. The speed with which viscosity increases is directly proportional to the rate at which air is being blown into the corn stillage oil, and indirectly proportional to the size of the air bubbles. The smaller the air bubbles, the more surface area the faster the reaction. The oil within the reactor is tested periodically to determine the viscosity at 40° C. of the blown oil. When the desired viscosity is obtained, the air sparging is stopped and the reactor is allowed to cool. Air is sparged through each of the samples for the times indicated in Table 3. The properties of the resulting blown oils are set forth in Table 3.

The properties of the resulting blown corn stillage oil are set forth below in Table 3.

TABLE 3

Properties of Blown Corn Stillage Oil

| Sample No. | 3-1 | 3-2 | 3-3 |
|---|---|---|---|
| Corn Stillage Oil Used | Sample 2-1 | Sample 2-1 | Sample 2-1a |
| Sparging Temperature (° C.) | 105 | 105 | 250 |
| Sparging Time (hours) | 23.5 | 42.5 | 14.5 |
| Viscosity@40° C. (cSt) | 63 | 220 | 526 |
| Viscosity@100° C. (cSt) | 12 | 34.7 | 56 |
| Viscosity Index | 192 | 206 | 173 |
| Flash Point (° C.) | 284 | 277 | 295 |
| Saponification Value (mg KOH/gram) | 190 | 200 | 192 |
| Pour Point Temperature (° C.) | −9 | −9 | −4 |
| Acid Value (mg KOH/gram) | 21 | 23 | 21 |
| Free Fatty Acid (wt %) | 10.5 | 11.5 | 10.5 |
| Iodine value (gram $I_2$/100 grams) | 120 | 102 | 83 |

TABLE 3-continued

Properties of Blown Corn Stillage Oil

| Sample No. | 3-1 | 3-2 | 3-3 |
|---|---|---|---|
| Gardner Color | 6 | 6 | >18 |
| Hydroxyl number (mg KOH/gram) | 9 | 53 | 43 |

As can be seen from Table 3, varying the amount and temperature of the corn stillage oil during sparging results in blown corn stillage oil having varying viscosities. The time required for blowing the corn stillage oils is relatively high, due to the large volume air bubbles utilized and the uneven dispersion of air bubbles within the reactor. A higher temperature was utilized to sparge Sample 3-3 to reduce the sparging time. If air was dispersed more evenly into the oil and the volume of the air bubbles was smaller, the temperature to manufacture a blown corn stillage oil having a similar viscosity as sample, 3-1 would preferably be reduced to between 105° C. and 115° C. With better dispersion of air bubbles within the corn stillage oil and smaller air bubbles, the required sparging time to produce samples having viscosities similar to those set forth in Samples 3-1 through 3-3, would be greatly reduced.

In addition, while not measured, the blown corn stillage oils of Table 3 are believed to contain less than one percent by weight titre.

Example 3

Stripping the Blown-Corn Stillage Oil

Into a 2000 glass reactor equipped with a stirrer, a heating mantel, a temperature regulator, a distillation column and a vacuum attachment 1200 grams of the blown corn stillage oil as indicated in Table 4 is charged. The blown corn stillage oil is stirred and a vacuum is drawn on the reactor (50 torr or less) and the reactor is heated to 250° C. The reactor is maintained under the vacuum at 250° C. to distill off free fatty acids and other low molecular weight components. The oil within the reactor is periodically tested for acid value. Once the acid value of the oil reaches the values indicated in Table 4, the stripping is ceased and the blown, stripped corn stillage oil is allowed to cool to ambient temperature. The properties of the resulting Blown, Stripped Corn Stillage Oil are set forth below in Table 4.

TABLE 4

Properties of Blown, Stripped Corn Stillage Oil

| Sample No. | 4-1 | 4-2 | 4-3 |
|---|---|---|---|
| Blown Corn Stillage Oil Used | 3-1 | 3-2 | 3-3 |
| 40° C. Viscosity (Pa · s) | 64 | 220 | 750 |
| 100° C. Viscosity (Pa · s) | 13 | 34.7 | 70 |
| Viscosity Index | 210 | 206 | 171 |
| Flash Point (° C.) | 293 | 298 | 323 |
| Saponification Value (mg KOH/gram) | 190 | 194 | 199 |
| Pour Point Temperature (° C.) | −10 | −14 | −6 |
| Acid Value | <5 | 4.5 | 3.8 |
| Free FattyAcid (wt %) | <2.5 | 2.2 | 1.9 |
| Iodine value (gram $I_2$/100 grams) | 120 | 102 | 83 |
| Gardner Color | 10 | 11 | >18 |
| Hydroxyl Value | 11 | 31 | 10 |
| Stripping Time (hours) | 1.5 | 1.5 | 1.0 |

The blown, stripped corn stillage oil of Sample 3-1 can be effectively used in general de-dust and lubrication end-use applications, such as bar and chain oil applications. The oil of Sample 3-2 exhibits a pour point temperature of −14° C.

and will be effective for use in low pour point applications. The blown, stripped corn stillage oil of Sample 3-1 with its relatively high flash point temperature and relatively high values of viscosity at 40° C. and 100° C. will be highly effective for end-use applications requiring high flash points.

In addition, while not measured, the blown, stripped corn stillage oils of Table 4 are believed to contain less than one percent by weight titre.

What is claimed is:

1. A method for producing a high viscosity, low volatiles blown-corn stillage oil, the method comprising the steps of:
   (a) obtaining a pressure-distilled corn stillage oil;
   (b) heating the oil to at least 90° C.;
   (c) passing air through the heated oil to produce a blown-corn stillage oil having a viscosity of at least 50 cSt at 40° C.;
   (d) stripping the blown corn stillage oil.

2. The method of claim 1 wherein the blown-corn stillage oil from step (c) exhibits a viscosity at 40° C. of at least 55 cSt and a viscosity at 100° C. of at least 11 cSt.

3. A method for producing a high viscosity, low volatiles blown-corn stillage oil, the method comprising the steps of:
   (a) obtaining a pressure-distilled corn stillage oil;
   (b) heating the oil to at least 90° C.;
   (c) passing air through the heated oil to produce a blown-corn stillage oil; and
   (d) stripping the blown corn stillage oil.

4. The method of claim 3, wherein the blown-corn stillage oil from step (c) has a viscosity of at least 650 cSt at 40° C. and a viscosity of at least 60 cSt at 100° C.

5. The method of claim 1, wherein the blown corn stillage oil has a viscosity of at least 60 cSt at 40° C.

6. The method of claim 1, wherein the blown corn stillage oil has a viscosity of at least 130 cSt at 40° C.

7. The method of claim 1, wherein the blown corn stillage oil has a viscosity of at least 5000 cSt at 40° C.

8. The method of claim 1, wherein the corn stillage oil comprises from 8 percent by weight to 16 percent by weight free fatty acids and the blown-corn stillage oil has at most 20 relative percent more free fatty acids than the corn stillage oil of step (a).

9. The method of claim 1, wherein the blown-corn stillage oil has at most 10 relative percent more free fatty acids than the corn stillage oil of step (a).

10. The method of claim 1, wherein the blown-corn stillage oil has equivalent free fatty acids as the corn stillage oil of step (a).

11. The method of any claim 1, wherein a time required to pass air through the corn-stillage oil in step (c) to obtain a blown-corn stillage oil having a particular viscosity at 40° C. is shorter than the time required to manufacture a blown soybean oil having equivalent viscosity under the same temperature and pressure conditions utilizing the same rate of passing air through the blown soybean oil as utilized for the blown corn stillage oil.

12. The method of claim 11, wherein the time required to obtain the blown-corn stillage oil is 25% less than the time to obtain the blown-soybean oil.

13. The method of claim 1, wherein air is sparged through the corn stillage oil in step (c) at a rate of from about 0.009 to 0.011 cubic feet per minute per pound oil.

14. The method of claim 3, wherein the blown-corn stillage oil from step (c) has a viscosity of at least 150 cSt at 40° C.

15. The method of claim 3, wherein the blown-corn stillage oil from step (c) has a viscosity of at least 200 cSt at 40° C.

* * * * *